United States Patent
Yang et al.

[11] Patent Number: 6,089,095
[45] Date of Patent: Jul. 18, 2000

[54] METHOD AND APPARATUS FOR NONDESTRUCTIVE INSPECTION AND DEFECT DETECTION IN PACKAGED INTEGRATED CIRCUITS

[75] Inventors: Ji Cheng Yang; Goh Jing Sua, both of Singapore, Singapore

[73] Assignee: Texas Instruments Incorporated, Dallas, Tex.

[21] Appl. No.: 08/994,727

[22] Filed: Dec. 19, 1997

[51] Int. Cl.[7] .................................................. G01N 29/06
[52] U.S. Cl. ............................ 73/600; 73/606; 73/620; 73/629
[58] Field of Search .............................. 73/579, 582, 587, 73/596, 597, 598, 606, 618, 619, 620, 627, 629, 646, 588, 599, 600, 602

[56] References Cited

U.S. PATENT DOCUMENTS

| | | | |
|---|---|---|---|
| 3,179,913 | 4/1965 | Mittler et al. | 339/18 |
| 3,370,203 | 2/1968 | Kravitz et al. | 317/101 |
| 3,459,998 | 8/1969 | Focarile | 317/100 |
| 3,904,934 | 9/1975 | Martin | 317/101 |
| 4,288,841 | 9/1981 | Gogal | 361/414 |
| 4,502,098 | 2/1985 | Brown et al. | 361/383 |
| 4,574,331 | 3/1986 | Smolley | 361/393 |
| 4,618,934 | 10/1986 | Nagase | 73/620 |
| 4,646,128 | 2/1987 | Carson et al. | 357/74 |
| 4,727,410 | 2/1988 | Higgins, III | 357/74 |
| 4,823,233 | 4/1989 | Brown et al. | 361/383 |
| 4,833,568 | 5/1989 | Berhold | 361/383 |
| 4,862,249 | 8/1989 | Carlson | 357/80 |
| 4,868,712 | 9/1989 | Woodman | 361/388 |
| 4,953,005 | 8/1990 | Carlson et al. | 357/80 |
| 5,016,138 | 5/1991 | Woodman | 361/381 |
| 5,019,945 | 5/1991 | Smolley | 361/412 |
| 5,303,590 | 4/1994 | Modderman et al. | 73/620 |
| 5,600,068 | 2/1997 | Kessler et al. | 73/620 |
| 5,627,320 | 5/1997 | Moore | 73/620 |
| 5,641,906 | 6/1997 | Moore | 73/614 |

*Primary Examiner*—Daniel S. Larkin
*Assistant Examiner*—Rose M. Miller
*Attorney, Agent, or Firm*—Mark E. Courtney; W. James Brady, III; Frederick J. Telecky, Jr.

[57] ABSTRACT

A method and apparatus for nondestructive inspection of packaged integrated circuits and defect detection in the integrated circuits. In a scanning acoustic microscopy system, a packaged integrated circuit under test 31 is placed in a tank containing an acoustic transmission medium such as de-ionized water. An acoustic reflector 29 is placed beneath the integrated circuit 31. A pulse-echo mode transducer 17 is used to scan the area containing the integrated circuit 31 with ultrasonic energy. The reflective signal energy is captured by the transducer 17 and the signals are digitized and stored. A computer system analyzes the reflective signal amplitude, and presents a visual image based on where the reflective signal was strong and where it was weak. In a preferred embodiment the image is presented so that the signal from the reflective plate is shown as a dark region where the reflection was weak or zero. It has been determined that those darkened areas will be areas where the integrated circuit under test has delamination or package cracking defects. The visual display can then be used by an operator, or alternatively the data could be analyzed by computer software in an automated system, to determine whether the packaged integrated circuit device under test contains delamination defects.

5 Claims, 2 Drawing Sheets

METHOD AND APPARATUS FOR NONDESTRUCTIVE INSPECTION AND DEFECT DETECTION IN PACKAGED INTEGRATED CIRCUITS

FIELD OF THE INVENTION

This invention relates generally to the inspection of packaged integrated circuits for the purpose of detecting defects such as delamination, package cracking, cracked die, material interface failures and other defects that can occur during or after the silicon die is packaged. Specifically, this invention relates to the use of acoustical scanning microscopy technology to inspect completed integrated circuits for these defects.

BACKGROUND OF THE INVENTION

In plastic packaging or molded packaging for integrated circuits, and in ceramic packaging of integrated circuits, a variety of materials are used. These materials are brought together in a die cavity inside a transfer or injection mold machine, and the package assembly is completed by molding the pieces together. After the molded package is created, the device is shipped to a customer. Traditionally, the integrated circuit had long leads extending from it which were inserted into a customers PC board for installation. Currently, the mounting technology for integrated circuits is moving towards surface mount technologies. In surface mounted systems, the integrated circuit is placed in close contact to the customers board on short gull wing or J type leads. The entire board including the integrated circuits is then processed through a solder reflow machine such as a vapor phase reflow system, or solder reflow oven, or other environments which expose the packaged integrated circuits to high temperatures.

During these high temperature processes, the mechanical tolerances within the packaged IC may be exceeded, resulting in thermal stress induced package failures. Some of these failures include package cracking, delamination at the die—encapsulant interfaces, delamination of die attach material, delamination of the lead frame tape from the die surface, and other defects. These defects are usually caused by the vaporization, under high temperatures, of moisture retained in the packaged IC. These defects can cause significant reductions in device reliability and in some cases can cause total device failure. Because this kind of failure happens at a stage where the part is being mounted in the customers system, the final result is that the board must be reworked and the defective part removed, the board made ready for further processing, and another part put into the board. The device failure may also occur after the board is installed in the end users system. At this stage such failures lead to expensive warranty exchanges, repair and rework.

In the prior art, packaged IC's were inspected destructively to detect such defects using probability and statistical analysis. Randomly sampled devices would be stressed in an test environment in an attempt to induce a delamination or package cracking defect. The devices would then have to be destructively taken apart by cross section and analyzed to see if a delamination defect occurred. Hopefully, no defects would be found, however in that case the test procedure has destroyed a reliable, functional device. If a defect is found, then additional sampling is needed to determine whether the lot of devices is suitable for shipping to the customer or not.

The current destructive sampling test procedures are lengthy in time, and cause the loss of devices that "pass" the test. Therefore nondestructive inspection methods have been developed. Typical inspection systems employ scanning acoustic microscopy (SAM) techniques. In a SAM system, acoustical energy is applied to a target device. The energy used is typically applied by a transducer which transmits in the ultrasound frequency range. A receiver is used to receive the signal reflections from the target device. The amplitude and phase information of the received signal may be converted into a visual display, or otherwise analyzed by computer or microprocessor or digital signal processor. Because certain structures are known to cause certain changes or attenuation in the signal, the amplitude and phase of the received signal may be used to identify certain physical structures in the target device.

It has been found that delamination or package cracking defects can be identified using SAM analysis. Although the molded IC package is opaque to visible light, the package material is transparent to sound energy which is in a range suitable for imaging internal interfaces. A large fraction of the incident sound energy is reflected at interfaces of materials, and especially at defects. The defects will usually include a void where one should not occur, and the void is usually filled with air. This will cause a reflection where one should not otherwise occur in a package without defects.

The acoustic probe in a conventional SAM system may be focused at a sufficiently small spot at the depth of certain features within the IC to resolve certain critical defect geometries and to inspect certain features. In performing reliability analysis, the technique is far superior to destructive testing because the test sample may be used again and again to take a variety of different measurements. Also, the same sample package can be subjected to many stresses and inspected to see when the first defects occur, thereby giving data on mean time between failures and lifetime expectancy for the package.

FIG. 1 depicts a prior art scanning acoustic microscope set up 10 for inspecting IC packages. A tank 11 contains de-ionized water as a transmission medium. Integrated circuit 13 is placed in the tank. A three axis positioning system 15 is used to move the transducer 17 about over the IC in the three directions X, Y and Z. The three axis positioning system 15 includes motor controller software running on computer 19, an external stepper motor driver 18 with microstepping capability, and three stages driven with individual stepper motors. Spike pulser/receiver 21 pulses the transducer 17 and receives the reflected energy, which is amplified and fed to a data acquisition board within the computer 19.

Computer 19 may include software for controlling the motors for the three axis positioning system, software to control and respond to the pulser receiver 21, and software to acquire data from the data acquisition board, perform data reduction, and provide visual display of the data acquired.

In operation, the planar lead frame and the co-planar and almost featureless packaging medium of the integrated circuit represent a favorable environment for inspection in SAM. The transducer 17 is used in the pulse echo or C-scan mode. A focused acoustic probe signal is scanned over the plane of the lead frame within the integrated circuit. The energy is transmitted into the tank 11 and into the package 13 in narrow ultrasonic pulses typically less than two periods in duration with a center frequency of 15–25 Mhz. The pulses are repeated at a relatively low repetition rate of 10–20 kHz to permit echo reception by the single transducer. De-ionized water is used as a transmission medium.

In one conventional system, the echo signal returning from the IC is digitized using analog to digital conversion circuitry at a sampling rate of up to 800 million samples/ second. The digitized data is reduced using software performing a data reduction algorithm and the resulting reduced parameters are stored in multiple buffers for use in developing images. Typically, an image representing a 3 cm×3 cm frame is scanned in less than 3 minutes. The image is then displayed on the display screen of the computer 19 for the operator or user.

Defects are easily identified using this system. To understand why this is so, a simple description of the mechanism for SAM is required. The prior art SAM system for identifying and locating package defects relies on the phenomenon of reflective signal phase inversion.

When the acoustic energy applied to the package 13 of FIG. 1 is reflected back towards the transducer, the signal phase may invert. This can be detected and displayed. A convenient model for this phenomenon is the model of plane sound waves striking, at a normal incidence, a planar boundary between two fluids. The reflection coefficient, R, is defined as the ratio of the amplitudes of the reflected and incident pressure waves:

$$R=(Z_2-Z_1)/(Z_2+Z_1) \quad \text{(Equation 1)}$$

The terms $Z_1$ and $Z_2$ are the characteristic acoustic impedances of the materials on the incident and the transmitted side of the material to material boundary, respectively. The characteristic acoustic impedance describes the coupling between the instantaneous pressure and particle velocity, and can be calculated from the equilibrium density, $\rho$, and plane wave speed, c. Thus for any particular impedance characteristic $Z_i$, $$Z_i=\rho_i c_i. \quad \text{(Equation 2)}$$

An examination of Equation 1 shows that the impedance mismatch across a boundary determines both the phase and the amplitude of the reflected pulse. For example, when the characteristic acoustic impedance of the second medium is less than that of the first medium, R is negative and the phase of the reflected pulse is inverted from the incident pulse. Also, the greater the difference between the acoustic impedances at the boundary, the greater the reflectivity of the boundary, that is the value for R will increase, so the reflected pulse will have a greater amplitude.

Typically in a packaged IC device, the acoustic impedance increases across a material interface. Examples are package to die interface, package to leadframe, die to tape interfaces. However, at a defect site, the acoustic impedance of the transmitted side of the boundary is less than that of the incident side, that is the encapsulant. This is a boundary between package material, usually plastic encapsulant or resin, and a void within the defect which is filled with air. Thus the interface is an encapsulant/air interface. Air has a very low relative acoustic impedance. Thus at this boundary, the reflected signal will exhibit a phase inversion. The acoustic receiver and data acquisition board can detect phase inversions in the reflected signal.

Experience with packaged integrated circuits has shown that the package material/silicon interfaces will show a greater intensity difference at delamination defect sites than at delamination defects occurring at package material/lead interfaces. However, if a material is present in the package that has a lower characteristic acoustic impedance Z than the package material, this internal interface will also cause a reflected signal phase inversion. The data analysis software operating in computer 19 will then have to use additional data and perform additional analysis in the temporal signal or the frequency domain signal in order to distinguish these phase inversions from delamination defects.

By performing time-of-flight analysis on the acoustic signal echo, it is possible in most cases to resolve the exact location of an internal interface within the package in three dimensions. Because the known internal interfaces can be exactly located, additional phase inversion interface sites can be classified as package defects. However, for some applications the conventional system of FIG. 1 is insufficient, or inappropriate. For example, some packaged IC's are provided in TSOP packaging, that is Thin Small Outline Packages. These packages are only around 1 mm thick when completely assembled. The normal SAM systems of the prior art cannot resolve small depths sufficiently to distinguish between defect sites and the expected internal package interface surfaces in the TSOP packages. Also, because the interfaces within the package and the defects both cause phase inversions in the reflected signal, several passes and several minutes of data reduction and software processing time is required for each image that is displayed. While the instrument described above is very useful for package development and failure analysis lab work, it is too slow and the data collection and reduction steps too awkward to use in a GO/NO-GO or PASS/FAIL type inspection station in a production environment. In producing IC's, it is desirable to have a time and cost efficient, simple to use, fast test station so that samples can be rapidly analyzed for pass or fail. In this kind of environment, it is not necessary to know exactly the location of a defect, so long as the defect can be generally classified. The operator of the equipment in a production environment is typically quite familiar with the package and so does not need to know exactly where the defect is located within the package, typically knowledge of the package type and the type of defect (e.g. cracking, delamination, die attach failure) will be enough information.

Finally, the conventional SAM system cannot analyze some IC packages now in volume production. In order to provide the SAM inspection of such packages, such as the very thin TSOP packages now in use, the existing equipment will have to be replaced with much more expensive SAM systems.

Accordingly, a need thus exists for a method and an apparatus for providing nondestructive scanning acoustical microscopy inspection for very thin I.C. packages and for pass fail reliability testing. The technique and apparatus should use existing systems and should provide a rapid processing and throughput capability for use in production environments.

SUMMARY OF THE INVENTION

Generally, and in one form of the invention, a reflective transmission technique and apparatus is disclosed for inspecting packaged integrated circuits for delamination defects. A scanning acoustic microscopy station is provided having an ultrasonic transducer and receiver acoustic probe, a sample tank usually filled with water, and a visual display for providing an image based on the reflections received by the acoustic probe. A reflective surface is provided underneath an integrated circuit under test. By transmitting pulses of ultrasonic energy through the integrated circuit, onto the reflective plate, back through the integrated circuit, and into the receiver, package delamination defects can be detected using an inexpensive, single transducer scanning acoustic microscope. These defects can be detected even in extremely thin package types, which are difficult or impossible to test using the scanning acoustic microscopy testing equipment of the prior art.

BRIEF DESCRIPTION OF THE DRAWINGS

In the drawings.

Corresponding numerals and symbols in the different figures refer to corresponding parts unless otherwise indicated in the specification and the figures.

DETAILED DESCRIPTION OF PREFERRED EMBODIMENT

Figure 2:
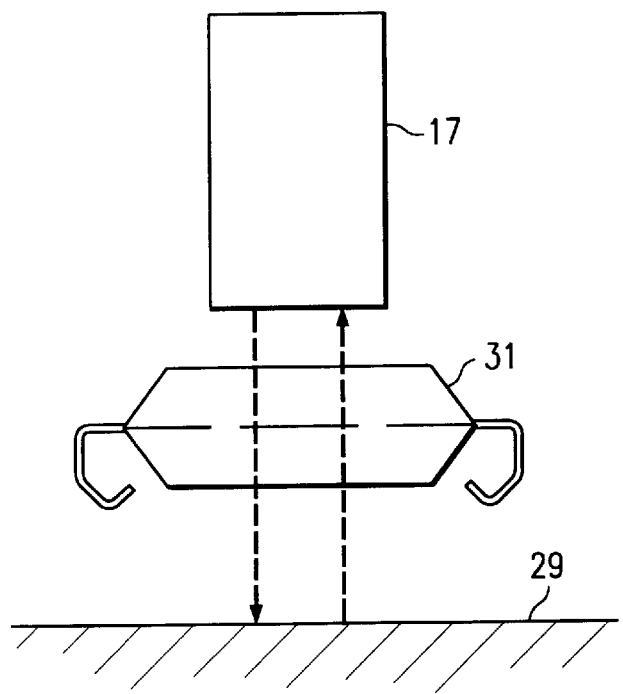
FIG. 2 depicts a view of a SAM test station using the apparatus and method of the invention.

FIG. 2 depicts the use of the SAM apparatus of the invention. An acoustic reflecting plate 29 is placed in the tank beneath the integrated circuit 31. Pulse echo energy is applied from transducer 17 and passes completely through the integrated circuit 31 and strikes the reflective plate 29. Part of ultrasonic energy strikes the plate 29 and is reflected back again passing through the integrated circuit and being received by the transducer pulser/receiver 17. The energy or signal amplitude of the reflected signal is directly related to the structure and properties of the IC package 31 and of course the reflective properties of the reflective plate 29. If defects such as delamination, package cracking, internal voids, material separation are present within the IC package under inspection, the reflected ultrasonic signal will not be able to go through the package 31 the second time and the transducer/receiver will receive a very weak reflected signal. As a result, by monitoring the reflected signals from the reflecting plate 29 at the transducer 17 and processing the signals into a visual image for display, the system can provide a visual indication that there are, or are not, delamination defects present in the package. In a preferred embodiment, the display system is programmed such that a special color is used to highlight the area where the reflected ultrasonic signal is close to zero, i.e. the area where the internal defects exist. In a less preferred embodiment, black is used on a black and white display to indicate that zero amplitude areas exist (e.g. no reflective signal is received and therefore a defect is indicated.)

Figure 3:
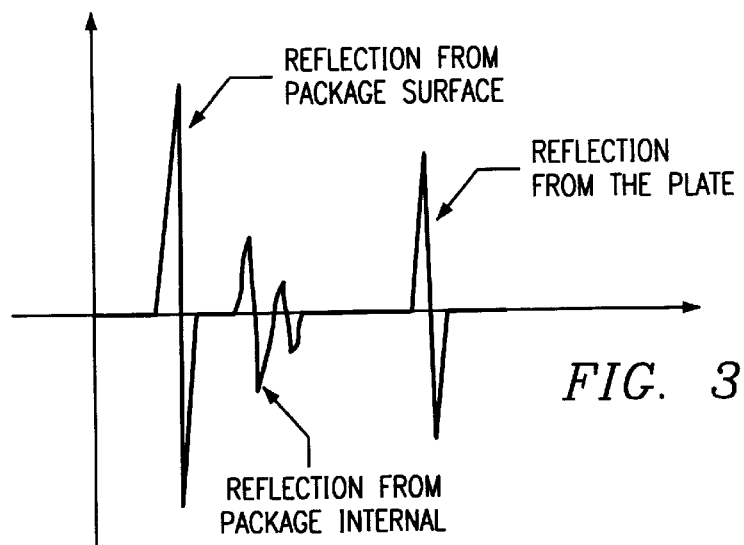
FIG. 3 is a graphical depiction of the reflected waveforms received by the transducer of the system of FIG. 2.

FIG. 3 is a demonstrative graph which indicates the typical signals received at the transducer when an integrated circuit is inspected. Three signals are received as reflections. The first is the strongest and is coming from the top surface of the package under inspection. The next signal, farther in distance and in time-of-fight, is from the internal planar leadframe and die within the package. The last signal which is typically stronger than the package internal signal is the reflected signal.

Figure 4:
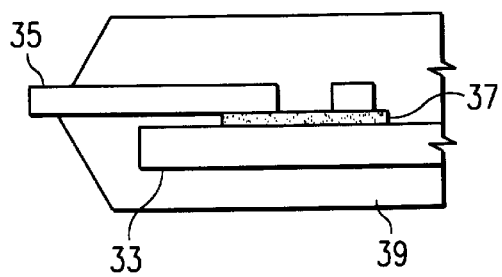
FIG. 4 depicts a TSOP integrated circuit package in cross section.

FIG. 4 depicts a cross sectional view of an integrated circuit in a TSOP package such as typically inspected with this system. Silicon die 33 is shown with a lead over chip or LOC leadframe 35 placed over the die. The die is physically coupled to the leadframe 35 using nonconductive adhesive tape 37. Bond wires, not shown, are used to couple the individual leads of the LOC leadframe to the center placed bond pads of the silicon die 33. The entire structure is then placed in a transfer mold press and encapsulated in mold compound, which is shown as 39 in FIG. 4.

Figure 1:
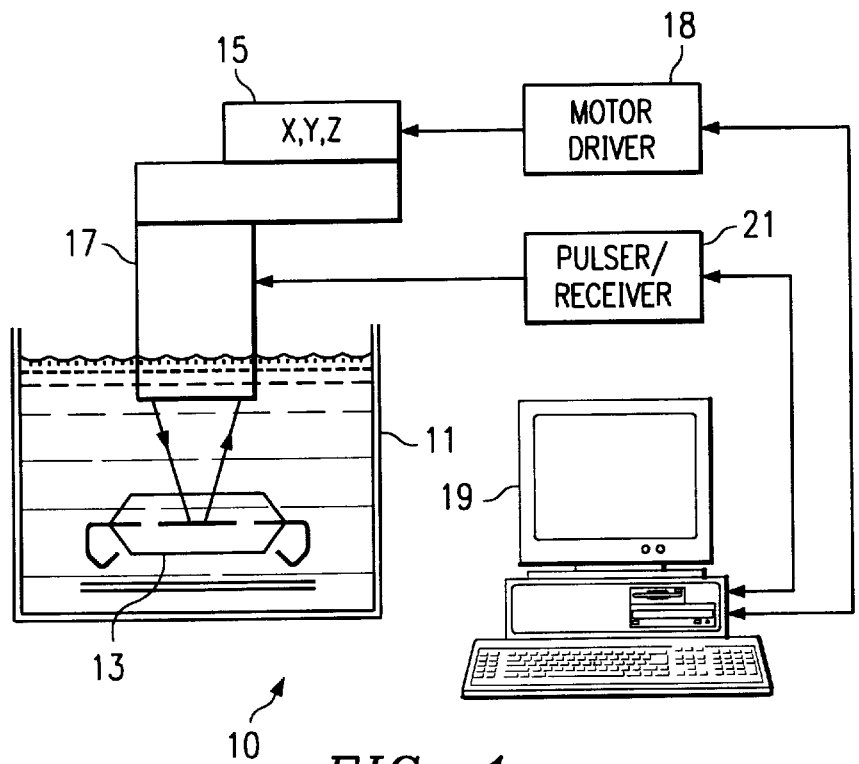
FIG. 1 depicts a prior art SAM test station which uses reflective signal phase inversion.

The package of FIG. 4 is a TSOP package used for memory devices, and is very thin, typically <1 mm when completed. There are several interfaces in the internal structure which will cause phase reversal in the reflected waves used by the conventional prior art SAM station of FIG. 1. Because the whole device is so thin, it is very difficult to use the conventional SAM station of FIG. 1 to analyze such a package for defects, because the reflections which arise from the mold compound/lead frame interface, the lead frame/tape interface, the tape/silicon die interface, and the silicon die/mold compound interface are close together physically. The reflective waves will be affected by these structures and these phase reversals are very difficult to separate and interpret in normal SAM pulse-echo systems. While more expensive SAM systems may work on these packages, this requires upgrading the existing SAM stations to handle thinner packages.

In contrast to the prior art systems, the TSOP type package of FIG. 4 can be analyzed easily using the apparatus and the method of the invention as shown in FIG. 2, without any equipment upgrades required. Because the reflective wave passes through the integrated circuit twice, the method is called "double through" SAM inspection. With the double through system of the invention, phase reversal is not relied upon to analyze the structure under test. Instead, the waves being reflected from the reflecting plate are analyzed on a signal strength or amplitude basis only, so that the phase reversals caused by the internal structure are not confused with defects, and also no extra resolution or signal processing is required to distinguish the internal structures from defects.

Figure 5:
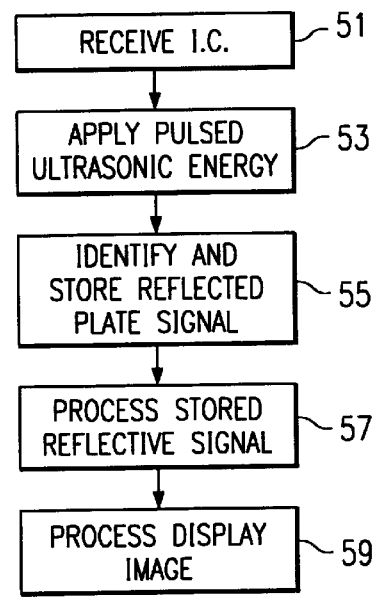
FIG. 5 depicts a. flow chart diagram of the steps comprising one embodiment of a method using the invention.

FIG. 5 depicts a flow diagram describing a preferred method of the invention. In FIG. 5, step 51 is to place the integrated circuit in a tank. The tank has a reflective plate at the bottom and contains de-ionized water. In step 53, the pulse echo transducer is used to apply ultrasonic energy to the tank. In step 55, the reflections are stored as the transducer scans the area of the integrated circuit being analyzed. In step 57, the data collected is readied for display. The signal reflected from the reflection plate, the so called "double through" signal, is identified by the time-of-fight or other analysis. The collected data points for this signal are then characterized into strong and weak reflections. The weak reflections or "zeros" are typically indicative of a delamination defect and are color coded for display on the operators display. In step 59, the operator makes a visual check on the display. If there are no defects, the visual display generally appears as an "X-ray" image of the internal structures of the integrated circuit. If there are package defects which stopped the reflective wave from the plate, these are shown as a dark or colored area on the image. The operator can then immediately make a "pass/fail" decision. Alternatively, an automatic system could be used which could count up or measure the amount of "zeros" in the reflective wave, and if the number of zeros exceeded a predetermined threshold, this system could determine that defects did exist in the device.

The method of FIG. 5 and the apparatus of FIG. 2 and the alternatives described above can also be used to look for delamination in structures the prior art cannot be used on, such as thin film on integrated circuits. A delamination defect area of some concern in the manufacture of dynamic random access memories, or DRAMs, is the delamination that can occur between the mold compound and the protective pix layer which is the top coating on the silicon die when it is completed. The conventional pulse-echo SAM system cannot separate the signals from other signals reflected from the package because the layers are so thin, only a few microns thick. Experiments with the "double through" technique of this invention show that this method and apparatus can detect these failures using the amplitude of the reflected wave from the reflective plate.

The method and apparatus of this invention as described above provide several advantages over the prior art pulse-echo SAM system that relies on phase reversal. First it can detect delamination in very thin structures or in very thin layers of materials. In contrast, the pulse-echo SAM systems of the prior art cannot resolve the signals.

Second, this method is faster than the prior art system. In order for the prior art system to distinguish the various internal structures present, several passes must be made with the acoustic probing signal focused at different depths. The multiple pass data must be stored, analyzed and correlated to get an image. In contrast, the present invention requires only a single scanning pass of the acoustic probe over the device under test, and is especially well suited for PASS/FAIL or GO/NO-GO testing in a production environment. This allows larger test samples and thus can greatly improve the reliability of the results. Since the only information needed in many applications is whether or not a defect exists, the invention is particularly advantageous over the prior art in these applications.

Third, the "double through" SAM system can detect delamination occurring at many different kinds of interfaces, including thin films such as pix/mold compound. In contrast, the prior art SAM system which relies on phase reversal to detect defects cannot distinguish some of these defects from the phase reversals caused by interfaces which are always present in integrated circuits.

The method and apparatus of the invention provides less information than that of the multiple pass pulse-echo mode SAM analysis of the prior art. This is only a disadvantage in an environment where the defect is being analyzed and studied, such as a failure analysis lab. In most applications, the detection of the defect is all that is required, and the invention is superior to the prior art in delamination defect detection. Further, the technique and apparatus of the invention may immediately be used with existing conventional pulse-echo SAM equipment, and as an additional advantage the conventional pulse-echo SAM equipment can also be used with the invention and in the slower, multiple pass, phase reversal analysis mode when necessary.

Figure 6:
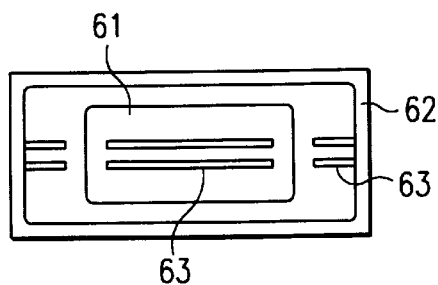
FIG. 6 depicts a sketch of a display typically presented to the operator when the system of the invention of FIG. 2 is used to examine an integrated circuit without defects.
Figure 7:
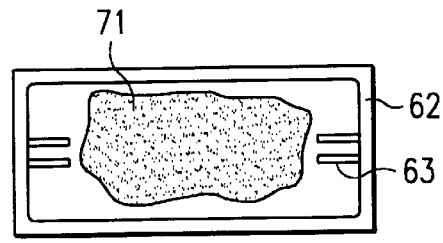
FIG. 7 depicts a sketch of a display typically presented to the operator when the system of the invention of FIG. 2 is used to examine an integrated circuit with defects.

FIGS. 6 and 7 are sketches depicting the typical display images which are presented to the operator of a SAM station when a non defective and a defective integrated circuit, respectively, are analyzed in a "double through" SAM system using the invention. In FIG. 6, an LOC TSOP package without delamination defects is presented. Because the reflective wave is present everywhere, the image appears as an internal view of the encapsulated package, showing the die 61, parts of the leadframe 63, the edge of the package 63 and other internal structures.

In FIG. 7, an image is sketched which resulted when a package was analyzed which had delamination defects intentionally created in it. The delamination was introduced by intentionally soaking the LOC tape for over one hundred hours prior to package assembly. The assembled device was exposed to IR solder reflow three times prior to the analysis. As was verified later by cross sectional analysis, the LOC tape delaminated during the three IR solder reflows. In FIG. 7, the image which appeared during the "double through" analysis is sketched. A black or darkened area 71 appears on the image where the reflected waves are not received, indicating the area affected by the delamination defects.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for nondestructive delamination defect detection in packaged integrated circuits, comprising the steps of:

providing a source of ultrasonic energy which can operate in a pulse-echo transmit/receiver mode;

providing a tank filled with an acoustic transmission medium placed beneath said source of ultrasonic energy;

providing an acoustic reflector within said tank;

providing an integrated circuit under test in said tank, such that said integrated circuit lies between said source of ultrasonic energy and said acoustic reflector;

scanning said integrated circuit with ultrasonic energy from said source by operating said source in a pulse echo mode while causing said source to travel over the area occupied by said integrated circuit;

detecting the reflected acoustic signal which travels through said integrated circuit, strikes said acoustic reflector and reflects, and travels back through said integrated circuit; and displaying the amplitude of said reflected acoustic signal as a visual image, with the strong areas of the reflected acoustic signal being a first color, and the weak areas of the reflected acoustic signal being a second color, the second color indicating the presence of a delamination defect in the package.

2. The method of claim 1, wherein said step of detecting the reflected acoustic signal further comprises:

detecting all acoustic signals reflected from said tank;

analyzing the acoustic signals using a time-of-flight temporal analysis; and identifying the reflected signals which were reflected by said acoustic reflector and traveled back through the integrated circuit to the energy source.

3. The method of claim 1 wherein the delamination defects detected are package cracking defects.

4. The method of claim 1, wherein the delamination defects detected are mold compound to pix delamination defects.

5. The method of claim 1, wherein the delamination defects detected are lead/frame tape delamination defects.

* * * * *